United States Patent [19]

Marwah et al.

[11] Patent Number: 5,869,709
[45] Date of Patent: Feb. 9, 1999

[54] PROCESS FOR EFFECTING ALLYLIC OXIDATION

[75] Inventors: Padma Marwah; Henry A. Lardy, both of Madison, Wis.

[73] Assignee: Humanetics Corporation, St. Louis Park, Minn.

[21] Appl. No.: 851,939

[22] Filed: May 7, 1997

[51] Int. Cl.[6] .................................. C07J 1/00; C07J 9/00; C07J 21/00; C07C 45/00
[52] U.S. Cl. ........................... 552/615; 552/542; 540/31; 568/232; 568/326; 560/129
[58] Field of Search ..................................... 552/615, 542; 540/31; 568/232, 326; 560/129

[56] References Cited

U.S. PATENT DOCUMENTS

| | | | |
|---|---|---|---|
| 4,263,215 | 4/1981 | Hesse et al. | 260/397.2 |
| 4,554,105 | 11/1985 | Hesse | 260/397.2 |

*Primary Examiner*—Jose' G. Dees
*Assistant Examiner*—Alton Pryor
*Attorney, Agent, or Firm*—Michael S. Sherrill

[57] ABSTRACT

A procedure for oxidizing organic compounds having allylic hydrogen atom(s) involving the steps of reactively contacting the organic compound with a combination of an alkali metal periodate and an alkyl hydroperoxide. The reaction can conveniently be conducted under ambient temperature and pressure conditions, and is conveniently conducted in a cosolvent system of water and organic solvent(s).

19 Claims, No Drawings

PROCESS FOR EFFECTING ALLYLIC OXIDATION

FIELD OF THE INVENTION

The invention relates to the allylic oxidation of organic compounds.

BACKGROUND

Allylic oxidation is a fundamental organic reaction of significant interest to organic chemists practicing in a variety of fields from agricultural products to pharmaceuticals. A variety of procedures are known for oxidizing various organic compounds that possess allylically activated hydrogen, but such procedures typically suffer from unsatisfactory yields, tedious workups and/or require the use of expensive and/or ecologically and physiologically undesirable reagents, such as chromium.

Hence, a continuing need exists for a simple, efficient, safe and cost effective procedure for selectively effecting allylic oxidation of organic compounds.

SUMMARY OF THE INVENTION

We have discovered a simple, efficient, safe, cost effective and ecologically friendly procedure for oxidizing organic compounds having allylic hydrogen atom(s). The procedure involves reactively contacting the organic compound with a combination of an alkali metal periodate and an alkyl hydroperoxide under conditions sufficient to effect oxidation of the allylic hydrogen(s) on the organic compound.

The reaction can conveniently be conducted under ambient temperature and pressure conditions, and is conveniently conducted in a cosolvent system of water and organic solvent(s).

DETAILED DESCRIPTION OF THE INVENTION INCLUDING A BEST MODE

Definitions

As utilized herein, including the claims, the term "allylic compound" references an organic compound having at least one allylic hydrogen atom.

As utilized herein, including the claims, the term "allylic oxidation" means oxidation of an allylic compound by replacing the allylic hydrogen(s) with oxygen or an oxygen containing group.

As utilized herein, including the claims, the term "reactants" collectively references allylic compound, alkali metal periodate and alkyl hydroperoxide. Solvents, including both organic solvent(s) and water, are specifically excluded from the definition of reactants.

As utilized herein, including the claims, "(v/v miscible)" refers to the volumetric percentage of water to total water miscible solvent(s).

Process

The process involves reactively contacting an allylic compound with an alkali metal periodate and an alkyl hydroperoxide under conditions sufficient to effect allylic oxidation of the allylic hydrogen atom(s) on the organic compound. For example, the allylic compound can be dissolved in a suitable mixture of a water miscible organic solvent, a water immiscible organic solvent and the alkyl hydroperoxide, and then incorporating the alkali metal periodate and a suitable amount of water into the reaction mixture. The water gradually dissolves the alkali metal periodate during the course of the reaction and thereby provides the necessary reactive contact between the reactants. As an added feature, the limited solubility of alkali metal periodate in water permits the pH of the reaction mixture to be controlled to some extent should such pH control be desired.

CONSTITUENTS

Allylic Compounds

Allylic compounds include any organic compound incorporating the structure —$C^1R=C^2H-C^3H_n$— within the molecule, wherein n is 1, 2 or 3. Hydrogen atoms attached to the $C^1$ and $C^2$ carbon atoms are referenced as vinylic hydrogen. Hydrogen atoms attached to the $C^3$ carbon atom are referenced as allylic hydrogen. The process of this invention selectively oxidizes allylic hydrogen atoms over vinylic hydrogen atoms. Exemplary allylic compounds include specifically, but not exclusively, (i) aliphatic vinylic compound such as methyl oleate, (ii) aromatic benzylic compounds such as fluorene and diphenyl methane, (iii) isoprenoids, such as carotenoids, terpenes, sesquiterpenes and vitamins, and (iv) steroids and sterols, such as androstenes, cholesterol, estraenes, pregnenes and derivatives thereof such as esters, ethers and ketals of these compounds.

Of particular commercial interest is the allylic oxidation of steroids, such as dehydroepiandrosterone and various derivatives of dehydroepiandrosterone, because the steroid can be allylically oxidized without the use of physiologically or ecologically hazardous materials, such as the transition metals. The invention does not contaminate the allylically oxidized product with a toxic metal.

Cooxidants (Alkali Metal Periodate and Alkyl Hydroperoxide)

A cooxidant system of an alkali metal periodate and an alkyl hydroperoxide is used to allylically oxidize the allylic compound. Experimentation has shown the specific combination of sodium periodate and butyl hydroperoxide can generally provide a superior yield and/or superior quality of allylically oxidized product under ambient reaction conditions. An additional benefit provided by the use of butyl hydroperoxide is that butyl hydroperoxide is a liquid under ambient conditions and can also facilitate dissolution of the allylic compound in the organic solvent(s).

Both the alkali metal periodate and alkyl hydroperoxide are available from a number of chemical suppliers. The alkyl hydroperoxide can be conveniently utilized in anhydrous form or as an aqueous solution. Since the reaction mixture preferably includes water for the purpose of gradually dissolving the alkali metal periodate during the course of the reaction, the alkyl hydroperoxide is most conveniently utilized as a 70 to 90 wt % aqueous solution.

Generally, a concentration of about 1 to about 5 mole equivalents alkali metal periodate, preferably about 1.5 to about 3 mole equivalents of alkali metal periodate, and about 10 to about 15 mole equivalents of alkyl hydroperoxide are effective for allylically oxidizing an allylic compound. Concentrations of less than about 1 mole equivalent of alkali metal periodate and less than about 10 mole equivalents of alkyl hydroperoxide significantly slows the reaction, while greater than about 3 mole equivalents of alkali metal periodate and greater than about 15 mole equivalents of alkyl hydroperoxide increases the cost of the process without producing a corresponding increase in any beneficial property or characteristic of the process or resultant product(s).

Organic Solvent(s)

The organic reactants (i.e. allylic compound and alkyl hydroperoxide) can be conveniently dissolved in suitable organic solvent(s). Depending upon the specific allylic compound and alkyl hydroperoxide used, the organic compounds may be suitably dissolved in a water miscible organic solvent(s), or may require the use of a biphasic organic solvent system which includes at least one water miscible organic solvent and at least one water immiscible organic solvent.

The water miscible solvent is selected primarily for its ability to dissolve the organic reactants and, when utilized in a biphasic system, to facilitate reactive contact between the water soluble alkali metal periodate and the organic reactants solubilized in the water immiscible organic solvent. Suitable water miscible organic solvents include specifically, but not exclusively, acetone, acetonitrile, t-butanol and organic bases such as pyridine.

The water immiscible solvent, when utilized, is selected primarily for its ability to dissolve the specific allylic compound to be oxidized and to create a clear biphasic reaction mixture. A variety of suitable water immiscible solvents are available, including specifically, but not exclusively: (i) aliphatic hydrocarbons, such as petroleum ether, n-hexane, n-heptane and iso-octane, and (ii) alicyclic hydrocarbons, such as cyclohexane.

Water

A sufficient amount of water is preferably incorporated into the reaction mixture for the purpose of controllably dissolving the alkali metal periodate throughout the course of the reaction. As previously referenced, the limited solubility of alkali metal periodate in water permits the pH of the reaction mixture to be controlled to some extent in those situations where pH control is necessary or desirable.

The reaction mixture can conveniently incorporate about 10% to about 50% (v/v miscible), preferably about 15% to about 40% (v/v miscible), most preferably about 20% to about 30% (v/v miscible), water. A concentration of less than about 10% (v/v miscible) significantly slows the rate of reaction, with a complete absence of water resulting in an almost complete absence of any allylic oxidation of the allylic compound.

PROCESSING PARAMETERS AND PROCEDURES

Reaction Time

While dependent upon a number of variables, including the specific allylic compound being oxidized, the specific cooxidants being used and the concentration of reactants within the reaction mixture, the reactions can typically be conducted in about 8 to about 48 hours.

Reaction Temperature

The reaction is preferably conducted under ambient conditions (i.e., temperatures between about 20° to 35° C.). We have found little incentive to actively heat or cool the reaction mixture. Temperatures below about 20° C. tend to slow the reaction rate without an observed increase in yield and/or quality of product, while temperatures above about 35° C. tend to reduce the yield and/or quality of desired oxidized product(s).

pH

The pH of the reaction mixture can impact the yield of desired product, with the optimal pH primarily dependent upon the specific allylic compound being oxidized. Alkali metal periodates are acidic reagents which tend to acidify the reaction mixture to a pH of approximately 5. In those cases where a more neutral pH is desired, such as when the allylic compound includes an acid sensitive group(s), the normally acidic pH of the reaction mixture can be neutralized to some extent by incorporating an organic base, such as pyridine, or a weak inorganic base, such as sodium bicarbonate, into the reaction mixture. Alternatively, the reaction can be conveniently carried out by using a solvent system of water and a water miscible organic base, such as pyridine.

Mixing

The reaction mixture should be continuously and vigorously stirred in order to promote contact between the reactants dissolved within the various solvents and thereby enhance the yield and/or quality of the desired allylically oxidized organic compound. In the absence of active mixing, we have observed a significant decrease in the yield and the quality of the desired product.

Solvent Dilution Factor

As with substantially any solvent-based reaction, the wt % solids should be retained between an upper solubility limiting percentage and a lower reaction rate limiting percentage. As the upper wt % of solids is reached, the viscosity of the resultant reaction mixture increases to such an extent that the necessary molecular interaction of the reactants are limited (e.g., the reaction mixture cannot be effectively mixed, with a resultant loss in yield and/or increased reaction time). Conversely, as the lower wt % of solids is reached, the reaction time begins to increase dramatically due to the reduced opportunity for the reactants to encounter one another within the reaction mixture. Such low concentrations of solids also results in increased expense due to the excessive amounts of solvent used per unit of reaction product obtained.

While the preferred wt % of solids in the reaction mixtures of this invention depend upon a number of variables, including the specific solvent(s) used and the specific reactants employed, a solids wt % of between about 5 to about 15 wt % has been found to be generally acceptable for producing a high yield of good quality product at a reasonable rate of reaction.

Separation and Purification Techniques

Upon completion of the oxidation reaction, the oxidized allylic organic compound can be separated from the solvent system, as well as any unused reactants and any byproducts, by any of a variety of techniques known to those skilled in the art including (i) dilution, (ii) filtration, (iii) extraction, (iv) evaporation, (v) distillation, (vi) decantation, (vii) crystallization/recrystallization, and/or (viii) chromatography.

The excess of alkyl hydroperoxide present in the system can be decomposed, when desired, by those methods known to those skilled in the art, such as (i) adding an aqueous solution of an alkali metal sulfite, (ii) adding a mixture of a mineral acid and acetic acid at a temperature of about 0° to 5° C., or (iii) adding a transition metal salt (e.g., ferrous amonium sulfate) in water.

The separated oxidized allylic organic compound can be further purified by various known techniques such as (i) washing the separated oxidized allylic organic compound with a solvent effective for selectively dissolving any remaining contaminants without dissolving appreciable quantities of the oxidized allylic organic compound, such as water or diethyl ether, and/or (ii) crystallizing the separated oxidized allylic organic compound in a suitable solvent or cosolvents.

EXAMPLES

Example 1

(Oxidation of 3β-Acetoxyandrost-5-ene-17-one (DHEAAc) to 3β-Acetoxyandrost-5-ene-7,17-dione (7-Oxo-DHEAAc)

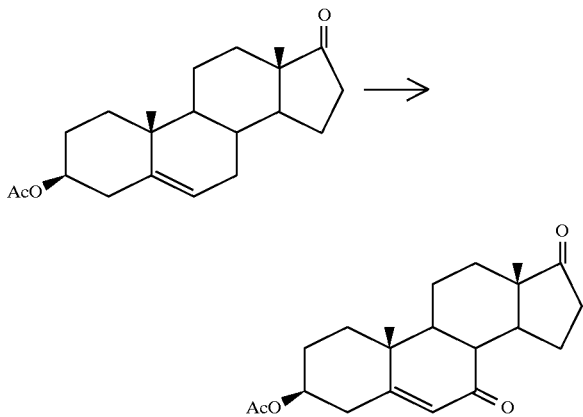

OXIDATION

3β-Acetoxyandrost-5-ene-17-one (DHEAAc) (50.0 g, 0.15 mol) was dissolved in a mixture of acetone (350 ml), petroleum ether (350 ml) and t-butyl hydroperoxide (70% aqueous solution, 200 ml). The mixture was stirred vigorously at room temperature and sodium periodate (42.6 g, 0.2 mol) and water (90 ml) added. After 16 hours of continuous stirring, an additional amount of sodium periodate (10.7 g, 0.05 mol) and water (20 ml) were added and the reaction mixture stirred continuously until the reaction had run to completion (TLC; Total 20 to 24 hours).

SEPARATION

The reaction mixture was then poured with stirring into a mixture of ice-water (3000 ml) and ethyl acetate (100 ml) and stirred for 1 hour, after which the mixture was suction filtered. The white crystalline solid material was washed thoroughly with water and dried under vacuum, yielding 29 grams of technical 7-oxo-DHEAAc having a melting point of 182°–184° C.

SECONDARY RECOVERY

The organic layer of the mother liquor was separated in a separatory funnel, washed well with water, and the solvent distilled off under reduced pressure. The resultant oily mass was dissolved in glacial acetic acid (100 ml) and cooled to 0°–5° C. Perchloric acid (60% solution, 2 ml) was added dropwise to the cooled solution and the solution stirred at this temperature for 15 minutes, after which it was poured into ice water. The aqueous layer was extracted with an ethyl acetate/petroleum-ether solvent system (2:1). The resultant organic phase was washed well with water and distilled. The residue was taken up in diethyl ether (100 ml) and held for 2 hours at −20° C. to form a crystalline precipitate. The crystalline material was filtered, washed with cold ether, and dried under suction to give an additional amount (6.2 grams) of 7-oxo-DHEAAc having a melting point of 182°–184° C.

YIELD

Total combined yield of 7-oxo-DHEAAc was 35.2 g (68.2%).

PURIFICATION AND CHARACTERIZATION

The total combined yield of 7-oxo-DHEAAc (35.2 grams) was recrystallized from methanol-water (300 ml, 5:1) to yield 30.0 g (58.14%) of pure crystalline 7-oxo-DHEAAc as white needles having a melting point of 185°–187° C. and the following NMR spectrum.

$^1$H NMR (CDCl$_3$, 200 MHz): δ 5.76 (d, J=1.4 Hz, 1H, 6H), 4.73 (m, 1H, 3α-H), 2.06 (s, 3H, COCH$_3$), 1.24 (s, 3H, 19-CH$_3$), 0.90 (s, 3H, 18-CH$_3$).

SIDE PRODUCTS

The organic filtrate was evaporated and chromatographed on silica gel (200–400 mesh) using ethyl acetate-petroleum ether as eluent. The side products identified below in Table 1 were isolated from the filtrate. The quantities of each side product are also listed below in Table 1.

TABLE 1

| NUMBER | QUANTITY (%) | FORMULA | SPECTRAL DATA |
|---|---|---|---|
| 1 | 3 |  | $^1$H NMR(CDCL$_3$, 200MHz)δ 5.7(s. 6, 7-H), 5.1(m, 3α-H), 2.03(s, COCH$_3$), 1.17(s, t-CMe$_3$), 0.97(s, 19-CH$_3$), 0.92(s, 18-CH$_3$); Mass: m/e 358(M—CH$_3$COOH), 329(M—OOtBu), 269(M—CH$_3$COOH, OOtBu), 270 (M—CH$_3$COO, OOtBu). |
| 2 | 5 |  | $^1$H NMR(CDCL$_3$): δ 5.68(d, J=4.8, 6-H), 4.68(m, 3α-H), 4.25(t, J=4.6, 7β-H), 2.047 (s, COCH$_3$), 1.21(s, t-CMe$_3$), 1.01(s, 19-CH$_3$), 0.86(s, 18-CH$_3$); Mass: m/e 329, 302 (M—CH$_3$COOH, CO, CH$_2$=CH$_2$), 269, 270. |

TABLE 1-continued

| NUMBER | QUANTITY (%) | FORMULA | SPECTRAL DATA |
|---|---|---|---|
| 3 | 5 (α 10%) (β 90%) | | $^1$H NMR(CDCL$_3$): δ 4.78(m, 3α-H), 3.15 (d, J=2.4Hz, 6-H), 2.037(s, COCH$_3$), 1.04 (s, 19-CH$_3$), 0.85(s, 18-CH$_3$), in case of α-epoxide 6-H comes at δ 3.5J=4.64Hz. |
| 4 | 2–5 a(α 30%) b(β 70%) | | $^1$H NMR(CDCL$_3$): δ 8.25(OOH, 4a), 8.08 (OOH, 4b), 5.74(d, J=6.2, 6-H(4a), 5.64(t, J=1.6Hz, 6-H(4b), 4.67(m, 3α-H), 4.28(dt, J=8.8, 2.0Hz, 7-H), 2.05(s, COCH3), 1.09 (s, 19-CH$_3$(4b), 1.03(s, 19-CH$_3$(4a), 0.9(s, 18-CH$_3$(4b), 0.88(s, 18-CH$_3$(4a). |
| 5 | 10–15 | | $^1$H NMR(CDCL$_3$): δ 5.66(d, J=4.8, 6-H), 4.63(m, 3α-H), 3.97(t, J=4.4Hz, 7β-H), 2.05(s, COCH$_3$), 1.04(s, 19-CH$_3$), 0.89(s, 18-CH$_3$). |

Example 2

(Oxidation of 3β-Acetoxyandrost-5-en-17-one (DHEAAc) to 3β-Acetoxyandrost-5-ene-7,17-dione (7-Oxo-DHEAAc)

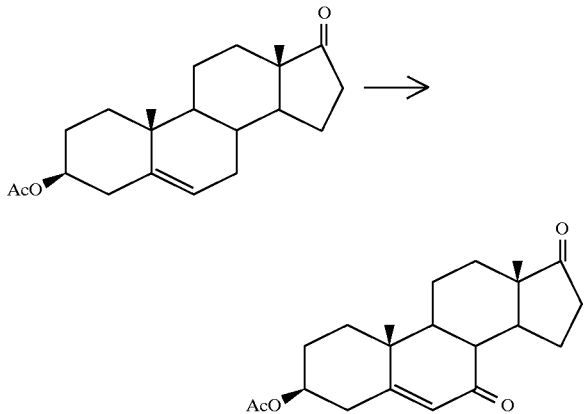

OXIDATION

3β-Acetoxyandrost-5-en-17-one (DHEAAC) (3.3 grams, 0.01 mol) was dissolved in a mixture of acetone (40 ml) and anhydrous t-butyl hydroperoxide (3M solution in 2,2,4-trimethylpentane, 50 ml). The mixture was stirred vigorously at room temperature and sodium periodate (10 grams, 0.046 mol) and water (10 ml) added. This biphasic reaction mixture was stirred continuously until the reaction had run to completion (16 hours).

SEPARATION

The reaction mixture was filtered through a bed of celite and acetone was removed from the residue under reduced pressure. The residue was dissolved in dichloromethane, washed with water and stirred with an aqueous sodium sulfite solution (10% aqueous solution, 50 ml) for 1 hour at room temperature. The organic layer was separated, washed with water, dried over anhydrous magnesium sulfate and solvent removed by distillation to form a crude material. The crude material was stirred with ether to afford a white crystalline material (2.2 grams).

SECONDARY RECOVERY

The mother liquor was chromatographed on silica-gel (70–230 mesh) using ethyl acetate-hexane (3:1) as eluent to yield an additional amount (0.3 gram) of 7-oxo-DHEAAc.

YIELD

Total combined yield of 7-oxo-DHEAAc was 2.5 g (72.7%).

PURIFICATION AND CHARACTERIZATION

The 7-oxo-DHEAAc (2.5 grams) was recrystallized from methanol-water (9:1) to yield 2.2 grams (63.95%) of pure crystalline 7-oxo-DHEAAc as white needles having a melting point of 185°–187° C.

Example 3

(Oxidation of 3β-Acetoxyandrost-5-ene-17-one (DHEAAc) to 3β-Acetoxyandrost-5-ene-7,17-dione (7-Oxo-DHEAAc)

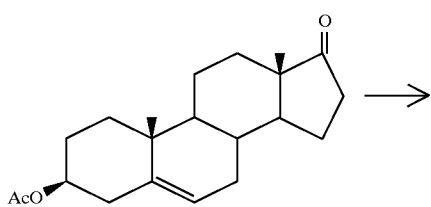

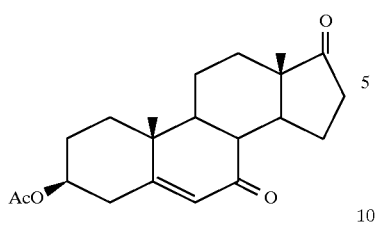
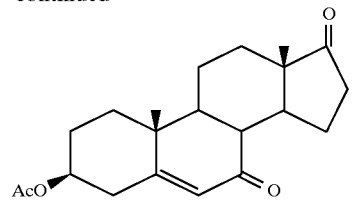

OXIDATION

3β-Acetoxyandrost-5-ene-17-one (DHEAAC) (3.3 grams, 0.01 mol) was dissolved in a mixture of t-butanol (35 ml), iso-octane (35 ml) and t-butyl hydroperoxide (70% aqueous solution, 20 ml). The mixture was stirred vigorously at room temperature and sodium periodate (6.62 grams, 0.03 mol) and water (9 ml) added. This biphasic reaction mixture was stirred continuously for 24 hours, at which time approximately 90% of the DHEAAc had reacted.

SEPARATION

The organic solvent was distilled off and the residue poured into ice water (200 ml), extracted with dichloromethane (30 ml), washed with water, dried and distilled to remove solvent. The residue was dissolved in diethyl ether (30 ml) and held for 2 hours at −20° C. to form a crystalline precipitate. The crystalline material was filtered, washed with cold ether, and dried under suction to yield 1.5 grams of 7-oxo-DHEAAc.

SECONDARY RECOVERY

The ethereal filtrate was shaken with a sodium sulfite solution (15% aqueous solution, 100 ml) for 2 hours at room temperature. The ether layer was separated, washed with water, dried and the solvent removed under suction. The resulting residue was dissolved in methanol (10 ml), held at −20° C. for 4 hours and filtered. The residue was dried to yield another 0.35 gram of 7-oxo-DHEAAc. It is noted that the residue could have alternatively been purified by column chromatography on silica gel (70–230 mesh) using hexane-ethyl acetate (3:1) as eluent.

YIELD

Total combined yield of 7-oxo-DHEAAc was 1.85 g (59.7% based upon 90% conversion).

PURIFICATION AND CHARACTERIZATION

The 7-oxo-DHEAAc (1.85 grams) was recrystallized from acetone-hexane to yield 1.75 grams (56.5% based upon 90% conversion) of pure crystalline 7-oxo-DHEAAc as white needles having a melting point of 184°–186° C.

OXIDATION

3β-Acetoxyandrost-5-ene-17-one (DHEAAc) (3.3 grams, 0.01 mol) was dissolved in a mixture of acetonitrile (35 ml), iso-octane (30 ml) and t-butyl hydroperoxide (70% aqueous solution, 20 ml). The mixture was stirred vigorously at room temperature and sodium periodate (6.42 grams, 0.03 mol) and water (9 ml) added. The reaction mixture was stirred continuously until the reaction had run to completion (15 hours).

SEPARATION

The acetonitrile and iso-octane were removed from the reaction mixture under reduced pressure and the resultant residue poured into a mixture of ice-water (200 ml) and dichloromethane (20 ml). The dichloromethane layer was separated, washed with water, and distilled to give crude 7-oxo DHEAAc. The crude 7-oxo DHEAAc was dissolved in ether and held at −20° C. for 2 hours to form a crystalline precipitate. The crystalline material was filtered, washed with cold ether, and dried under suction to yield 7-oxo-DHEAAc (1.9 g).

SECONDARY RECOVERY

The ethereal mother liquor was added to a solution of sodium sulfite (15% aqueous solution, 100 ml) and stirred for 2 hours at room temperature to decompose any excess t-butyl hydroperoxide. The ether layer was separated, washed twice with water, dried and distilled to produce a crude oily mass. The crude oily mass was chromatographed on silica gel (70–230 mesh) and the product eluted with 25% (v/v) ethyl acetate in hexane to give another 0.35 gram of 7-oxo-DHEAAc.

YIELD

Total combined yield of 7-oxo-DHEAAc was 2.25 grams (65.4%).

PURIFICATION AND CHARACTERIZATION

The 7-oxo-DHEAAc (2.25 grams) was recrystallized from methanol-water (98:2) to yield 1.95 g (56.6%) of pure crystalline 7-oxo-DHEAAc as white needles having a melting point of 185°–186° C.

Example 4

(Oxidation of 3β-Acetoxyandrost-5-ene-17-one (DHEAAc) to 3β-Acetoxyandrost-5-ene-7,17-dione (7-Oxo-DHEAAc)

Example 5

(Oxidation of 3β-Acetoxyandrost-5-en-17-one (DHEAAc) to 3β-Acetoxyandrost-5-ene-7,17-dione (7-Oxo-DHEAAc)

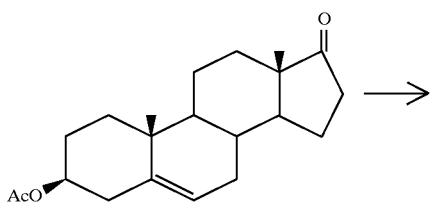
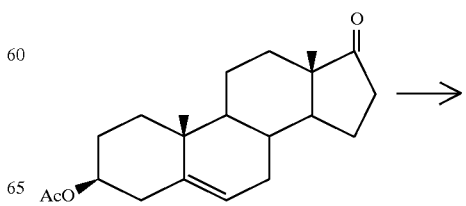

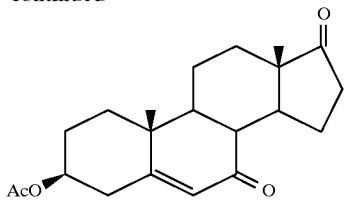

OXIDATION

3β-Acetoxyandrost-5-en-17-one (DHEAAc) (0.33 g, 0.001 mol) was dissolved in a mixture of acetone (4 ml), heptane (3.5 ml) and t-butyl hydroperoxide (70% aqueous solution, 2 ml). The mixture was stirred vigorously at room temperature and sodium periodate (0.64 gram, 0.003 mol), water (0.5 ml) and pyridine (0.2 ml) was added. The reaction mixture was stirred continuously for 16 hours until the reaction had run to completion.

SEPARATION

The organic solvent was removed from the reaction mixture under reduced pressure and the resultant mass poured into ice water (200 ml) and extracted twice with a mixture of ethyl acetate-hexane (30 ml, 1:1). The combined extracts were stirred with an aqueous sodium bisulfite solution(5% aqueous solution, 100 ml) for 2 hours at room temperature. The organic layer was separated, washed with water, dried and distilled to form a crude material. The crude material was stirred with ether and cooled for 2 hours to produce white crystalline 7-oxo-DHEAAc. The crystalline 7-oxo-DHEAAc was filtered, washed with cold ether and dried to afford 0.18 gram of 7-oxo-DHEAAc.

The filtrate was concentrated and chromatographed on silica gel (70–230). The product was eluted with ethyl acetate-hexane (1:3) to yield an additional 0.04 gram of 7-oxo-DHEAAc.

YIELD

Total combined yield of 7-oxo-DHEAAc was 0.22 gram (64%).

PURIFICATION AND CHARACTERIZATION

The 7-oxo-DHEAAc (0.22 gram) was recrystallized from ethanol-water to yield 0.19 gram (55.2%) of pure crystalline 7-oxo-DHEAAc as white needles.

Example 6

(Oxidation of 3β-Acetoxyandrost-5-ene-17-one (DHEAAc) to 3β-Acetoxyandrost-5-ene-7,17-dione (7-Oxo-DHEAAc)

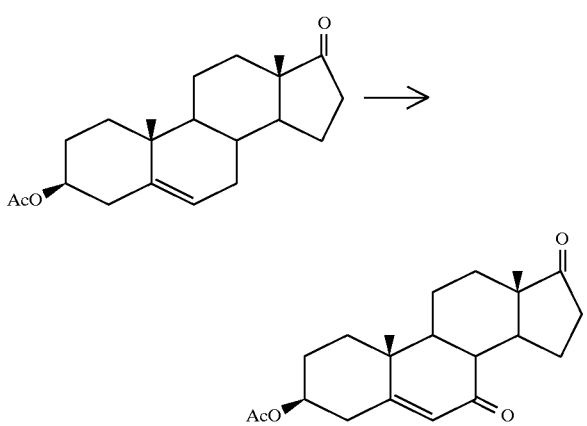

OXIDATION

3β-Acetoxyandrost-5-ene-17-one (DHEAAC) (0.33 g, 0.001 mol) was dissolved in a mixture of pyridine (3 ml), water (2 ml) and t-butyl hydroperoxide (90% aqueous solution, 2 ml). The mixture was stirred vigorously at room temperature and sodium periodate (0.64 gram, 0.003 mol) was added. The reaction mixture was stirred continuously for 8 hours until the reaction had run to completion.

SEPARATION

The reaction mixture was poured into ice water and the oxidation product extracted with ethyl acetate-hexane (1:1). The organic layer was separated, stirred with an aqueous sodium sulfite solution (15% aqueous solution, 10 ml), washed with water, dried and distilled. The crude product was triturated with diethyl ether and held for 4 hours at −20° C. to form a crystalline precipitate. The crystalline material was filtered, washed with ether and dried to yield 0.23 gram of 7-oxo-DHEAAc (66.8%)

YIELD

Total yield of 7-oxo-DHEAAc was 0.23 gram (66.8%).

PURIFICATION AND CHARACTERIZATION

The 7-oxo-DHEAAc (0.23 gram) was recrystallized from acetone-hexane (8:2) to yield 0.21 gram (61%) of pure crystalline 7-oxo-DHEAAc as white needles having a melting point of 183°–185° C.

Example 7

(Oxidation of 3β-ol-androst-5-en-17-one (DHEA) to 3β-ol-androst-5-ene-7,17-dione (7-Oxo-DHEA)

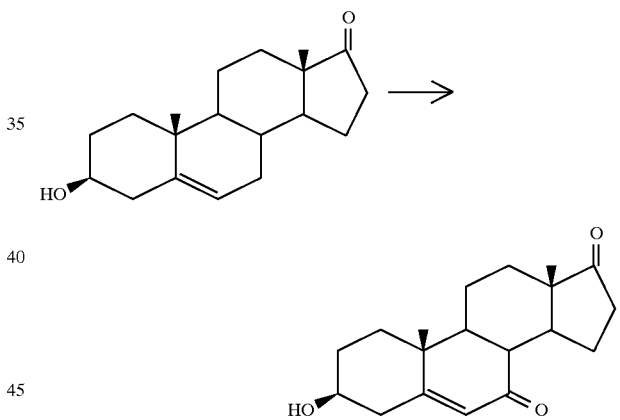

OXIDATION

3β-ol-androst-5-en-17-one (DHEA) (1.44 grams, 0.005 mol) was dissolved in a mixture of acetone (10 ml), petroleum-ether (10 ml) and t-butyl hydroperoxide (70% aqueous solution, 10 ml). The mixture was stirred vigorously at room temperature and sodium periodate (3.0 grams, 0.014 mol) added. The reaction mixture was stirred continuously until the reaction had run to completion (8 hours).

SEPARATION

The reaction mass was poured into ice-water and stirred continuously for 1 hour. The mixture was then cooled for an additional 2 hours at 0° to 5° C. to form a crystalline precipitate. The crystalline material was filtered under suction, washed with water and then with cold ether, and dried to yield 0.65 gram of 7-oxo-DHEA.

The organic layer of the filtrate was separated from the aqueous layer and washed with an aqueous sodium sulfite solution (10% aqueous solution), aqueous sodium bicarbonate and water. The solvent was removed by a rotary evaporator and the resulting residue chromatographed on a short column of silica gel (70–230) using hexane-ethyl acetate (60:40) as eluent to yield an additional amount (0.3 gram) of 7-oxo-DHEA.

YIELD

Total combined yield of 7-oxo-DHEA was 0.95 gram (62.9%).

PURIFICATION AND CHARACTERIZATION

The 7-oxo-DHEA (0.95 gram) was recrystallized from methanol to yield 0.8 g (53%) of pure crystalline 7-oxo-DHEA as white needles having a melting point of 238°–240° C. and the following NMR spectrum.

$^1$H NMR (CDCl$_3$, 200 MHz): δ 5.75 (d, J=1.4 Hz, 1H, 6H), 3.68 (m, 1H, 3α-H), 1.23 (s, 3H, 19-CH$_3$), 0.90 (s, 3H, 18-CH$_3$).

Example 8

(Oxidation of 3β,17β-diacetoxyandrost-5-ene to 3β, 17β-diacetoxyandrost-5-ene-7-one

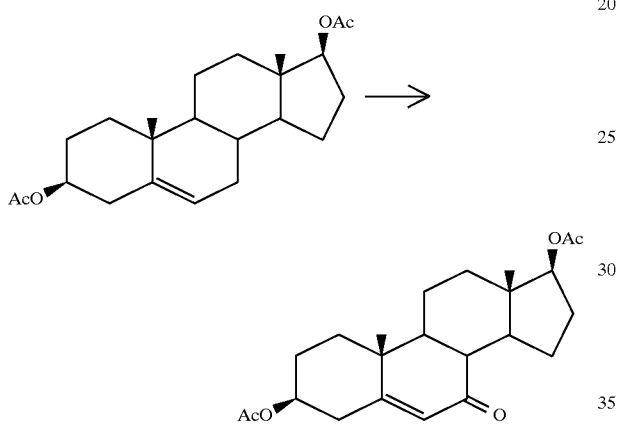

OXIDATION

3β,17β-Diacetoxyandrost-5-ene (1.12 grams, 0.003 mol) was dissolved in a mixture of acetone (12 ml) and t-butyl hydroperoxide (anhydrous, 3M solution in 2,2,4-trimethylpentane, 15 ml). The mixture was stirred vigorously at room temperature and sodium periodate (1.92 grams, 0.009 mol) and water (3 ml) added. This biphasic reaction mixture was stirred continuously for 16 hours at room temperature until the reaction had run to completion.

SEPARATION

The solvent was removed under reduced pressure and the resulting residue diluted with dichloromethane (10 ml). The dichloromethane layer was washed thoroughly with water and then stirred with an aqueous sodium sulfite solution (15% aqueous solution, 30 ml) for 2 hours. The organic layer was separated, washed with water, evaporated to dryness, and the resultant crude product dissolved in ether and held for 4 hours at –20° C. to form a crystalline precipitate. The crystalline material was collected under suction, washed with cold ether, and dried to yield 0.76 gram of 3β, 17β-diacetoxyandrost-5-ene-7-one.

SECONDARY RECOVERY

The mother liquor was chromatographed on silica-gel (70–230 mesh) using ethyl acetate-hexane as eluent to yield an additional amount (0.15 gram) of 3β, 17β-diacetoxyandrost-5-en-7-one having a melting point of 222°–224° C.

YIELD

Total combined yield of 3β, 17β-diacetoxyandrost-5-en-7-one was 0.91 gram (78.4%).

CHARACTERIZATION

The 3β, 17β-diacetoxyandrost-5-en-7-one had a melting point of 222–°224° C. and the following NMR spectrum.

$^1$H NMR (CDCl$_3$, 200 MHz): δ 5.72 (d, J=1.4 Hz, 1H, 6H), 4.69 (m, 2H, 3α-H & 17α-H), 2.05 (s, 3H, COCH$_3$), 2.045 (s, 3H, COCH$_3$), 1.22 (s, 3H, 19-CH$_3$), 0.81 (s, 3H, 18-CH$_3$).

Example 9

Oxidation of 3β,17β-diacetoxyandrost-5-ene to 3β, 17β-diacetoxyandrost-5-ene-7-one

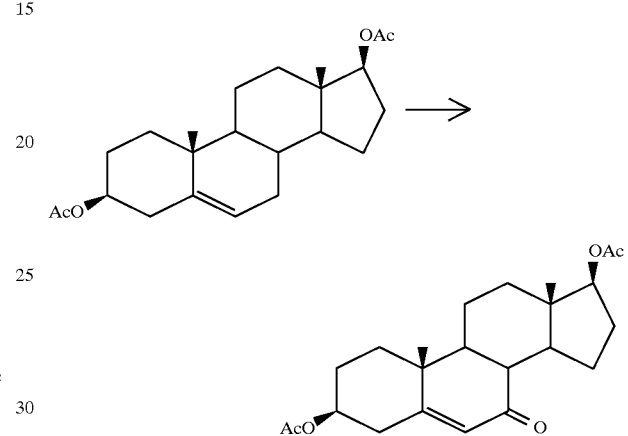

OXIDATION

3β,17β-diacetoxyandrost-5-ene (1.87 grams, 0.005 mol) was dissolved in a mixture of acetone (20 ml), isooctane (15 ml) and t-butyl hydroperoxide (70% aqueous solution, 10 ml). The mixture was stirred vigorously at room temperature and sodium periodate (3.2 grams, 0.015 mol) and water (3 ml) added. This biphasic reaction mixture was stirred continuously at room temperature until the reaction had run to completion (24 hours).

SEPARATION

The solvent was removed under reduced pressure and the resulting residue diluted with dichloromethane (10 ml). The dichloromethane layer was washed thoroughly with water and then stirred with an aqueous sodium sulfite solution (15% aqueous solution, 30 ml) for 2 hours. The organic layer was separated, washed with water, evaporated to dryness, and the resultant crude product dissolved in ether and held for 4 hours at –20° C. to form a crystalline precipitate. The crystalline material was collected under suction, washed with cold ether, and dried to yield 1.48 grams (76.28%) of 3β, 17β-diacetoxyandrost-5-ene-7-one having a melting point of 222°–224° C.

SECONDARY RECOVERY

The mother liquor was chromatographed on silica-gel (70–230 mesh) using ethyl acetate-hexane as eluent to yield an additional amount (0.07 gram) of pure 3β, 17β-diacetoxyandrost-5-ene-7-one.

YIELD

Total combined yield of 3β, 17β-diacetoxyandrost-5-ene-7-one was 1.55 grams (79.8%).

Example 10

Oxidation of 3β-acetoxycholest-5-ene (CholesterylAc) to 3β-acetoxycholest-5-ene-7-one (7-Oxo-CholesterylAc)

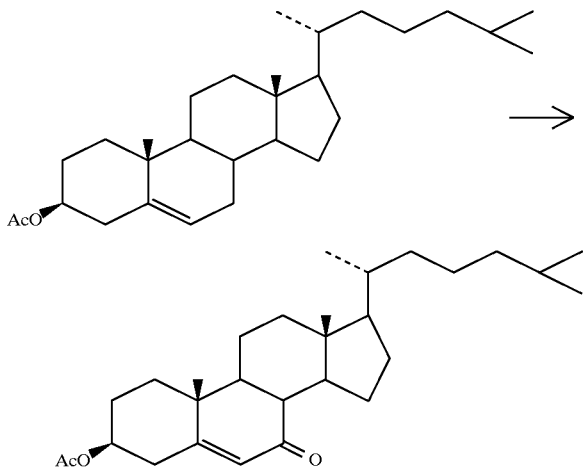

OXIDATION

Cholesteryl acetate (2.14 grams, 0.005 mol) was dissolved in a mixture of acetone (40 ml), isooctane (30 ml) and t-butyl hydroperoxide (70% aqueous solution, 10 ml). The mixture was stirred vigorously at room temperature until clear, and then sodium periodate (3.21 grams, 0.015 mol) and water (7 ml) were added slowly. This biphasic reaction mixture was stirred continuously for 24 hours at room temperature, at which time more than 90% of the starting materials had reacted.

SEPARATION

The acetone was removed under reduced pressure and the residue dissolved in dichloromethane. The resultant organic layer was washed with copious amounts of water and distilled to form a crude material. The crude material was dissolved in methanol (20 ml) and filtered. The filtrate was held for 4 hours at −20° C. to form a crystalline solid. The crystalline material was collected under suction, washed with cold methanol, and dried to yield 1.4 grams of 7-oxo-cholesteryl acetate having a melting point of 155°–156° C.

SECONDARY RECOVERY

The organic filtrate was concentrated, taken up in diethyl ether (20 ml) and stirred with an aqueous sodium sulfite solution (15% aqueous solution, 50 ml) for 2 hours. The ether layer was separated, washed with water, dried, and chromatographed on silica-gel (70–230 mesh) using ethyl acetate-hexane (1:9) as eluent to yield an additional amount (0.15 gram) of 7-oxo-cholesteryl acetate.

YIELD

Total combined yield of 7-oxo-cholesteryl acetate was 1.55 grams (78.0% based upon 95% conversion).

CHARACTERIZATION

The 7-oxo-cholesteryl acetate had a melting point of 155°–157° C. (melting point for compound listed at 155°–156° C. in A. H. Milburn, E. V. Truter and F. P. Woodford, J. Chem. Soc., 1956, 1740) and the following NMR spectrum.

$^1$H NMR (CDCl$_3$, 200 MHz): δ 5.7 (d, J=1.0 Hz, 1H, 6H), 4,72 (m, 1H, 3α-H), 2.05 (s, 3H, COCH$_3$), 1.21 (s, 3H, 19-CH$_3$), 0.91 (d, J=7.2 Hz, 3H, 21CH$_3$), 0.88 & 0.84 (2s, 6H, 26,27-CH$_3$), 0.68 (s, 3H, 18-CH$_3$).

Example 11

Oxidation of 3β-acetoxy-17,17-ethylenedioxyandrost-5-ene to 3β-acetoxy-17,17-ethylenedioxyandrost-5-en-7-one

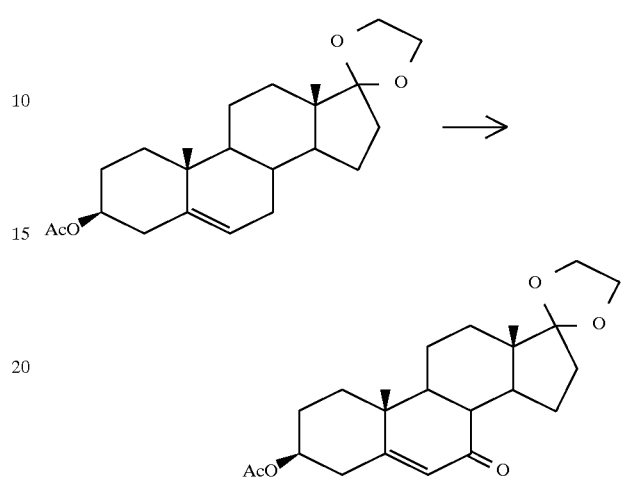

OXIDATION

3β-acetoxy-17,17-ethylenedioxyandrost-5-ene (0.374 gram, 0.001 mol) was dissolved in a mixture of acetone (3.5 ml) and heptane (3.5 ml). Aqueous t-butyl hydroperoxide (70% aqueous solution, 2 ml) was added to the solution and the resultant solution stirred at room temperature for 15 minutes, after which sodium periodate (0.65 gram, 0.003 mol), water (0.9 ml) and sodium bicarbonate (0.055 gram) were added in succession. This reaction mixture was stirred continuously at room temperature until the reaction had run to completion (14 hours).

SEPARATION

The reaction mixture was diluted with ethyl acetate (10 ml) and then sequentially washed with excess water, twice with an aqueous sodium sulfite solution (15% aqueous solution), and water. Evaporation of the solvent yielded 0.31 gram of a white solid having a melting point of 180°–182° C.

PURIFICATION AND CHARACTERIZATION

The 3β-acetoxy-17,17-ethylenedioxyandrost-5-en-7-one was recrystallized from methanol to yield 0.26 gram (67.0%). of pure crystalline 3β-acetoxy-17,17-ethylenedioxyandrost-5-en-7-one as white needles having a melting point of 182°–183° C. (melting point for compound listed in the literature as 175°–177° C. in Fieser L. R.-JACS 76, 1945, (1954)) and the following NMR spectrum.

$^1$H NMR (CDCl$_3$, 200 MHz): δ 5.7 (d, J=1.4 Hz, 6H), 4.7 (m, 1H, 3α-H), 3.87 (m, 6H, CH$_2$-ketal), 2.06 (s, 3H, COCH$_3$), 1.21 (s, 3H, 19-CH$_3$), 0.87 (s, 3H, 18-CH$_3$).

Example 12

Oxidation of Diphenyl Methane to Benzophenone

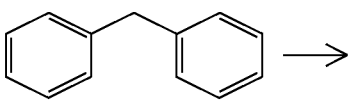

17
-continued

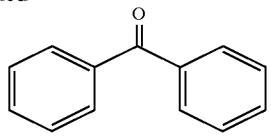

OXIDATION

Diphenyl methane (3.36 grams, 0.02 mol) was dissolved in a mixture of acetone (30 ml), petroleum ether (30 ml), t-butyl hydroperoxide (70% aqueous solution, 20 ml) and water (9 ml). The mixture was stirred vigorously at room temperature and sodium periodate (6.42 grams, 0.03 mol) added. This biphasic reaction mixture was stirred continuously for 48 hours at room temperature, at which time 90% of the starting materials had reacted.

SEPARATION

The solvent was removed by evaporation under water pump suction. The resulting residue was stirred with an aqueous sodium sulfite solution (15% aqueous solution, 100 ml) for 2 hours. The resulting product was extracted with diethyl ether and washed twice with water.

The organic phase was dried over magnesium sulfate and evaporated. The residue was chromatographed on a column of silica gel (70–230 mesh) and eluted with ethyl acetate (0 to 3% (v/v)) in hexane. The fractions eluted with hexane were combined and distilled to yield 0.30 gram of unreacted diphenyl methane. The ethyl acetate-hexane fractions were combined and evaporated to yield benzophenone as a white oil (3.0 grams).

YIELD

Total yield of benzophenone was 3.0 grams (92.4% based upon 90% conversion).

CHARACTERIZATION

The benzophenone had the following NMR spectrum.

$^1$H NMR (CDCl$_3$, 200 MHz): δ 7.43–7.64 and 7.78–7.84 (m, 10H, ArH).

Example 13

Oxidation of Fluorene to Fluorenone

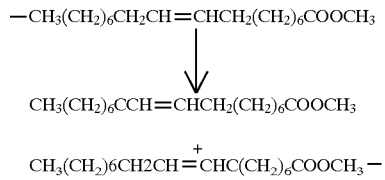

OXIDATION

Fluorene (1.66 grams, 0.01 mol) was dissolved in a mixture of acetone (40 ml), heptane (30 ml), t-butyl hydroperoxide (70% aqueous solution, 20 ml) and water (4 ml). The resultant solution was stirred at room temperature for 15 minutes, after which sodium periodate (4.26 grams, 0.02 mol) was added. This reaction mixture was stirred continuously at room temperature until the reaction had run to completion (16 hours).

SEPARATION

The solvent was removed under vacuum and diethyl ether (20 ml) added to the residue. The organic layer was separated, washed with copius amounts of water and then stirred with an aqueous sodium sulfite solution (15% aqueous solution, 100 ml) for 2 hours at room temperature. The ether layer was separated, washed with water, dried and distilled to yield fluorenone. The fluorenone was dissolved in ethanol (95%) and held for 2 hours at −10° C. to form a crystalline solid. The pale yellow crystals of fluorenone were filtered, washed with cold ethanol, dried under suction and then dried in a vacuum desiccator for 2 hours to yield fluorenone (1.71 grams)

YIELD

Total yield of fluorenone was 1.71 grams (95.0%).

CHARACTERIZATION

The fluorenone had a melting point of 82°–84° C. (melting point for compound listed at 82°–85° C. in the Aldrich Catalogue) and had the following NMR spectrum.

$^1$H NMR (CDCl$_3$, 200 MHz): δ 7.67 (t), 7.64 (t), 7.5 (m) and 7.29 (m) 8H, ArH

Example 14

Oxidation of Methyl 9-octadecenoate to a Mixture of the Isomers

Methyl 8-oxo-9-octadecenoate and Methyl 11-oxo-9-octadecenoate

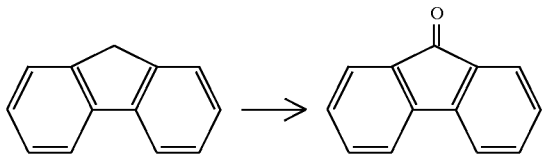

OXIDATION

Methyl oleate (1.1 grams, 0.0029 mol) was dissolved in a mixture of acetone (3.2 ml), heptane (3.0 ml), t-butyl hydroperoxide (70% aqueous solution, 3 ml) and water (0.45 ml). The resultant solution was stirred at room temperature and sodium periodate (0.94 gram, 0.0044 mol) was added. This reaction mixture was stirred continuously for 36 hours at room temperature then quenched with water, at which time 58% of the starting materials had reacted.

SEPARATION

The quenched reaction mixture was extracted with diethyl ether and sequentially washed with water, an aqueous sodium sulfite solution (15% aqueous solution), and water. The organic layer was dried over magnesium sulfate and evaporated under reduced pressure. The resulting oily residue was chromatographed on a column of silica gel (70–230) and eluted with ethyl acetate (0 to 5% (v/v)) in petroleum ether. The fractions eluted with pure petroleum ether were combined and distilled to yield 0.46 gram (41.8%) of unreacted methyl oleate. The fractions eluted with 5% (v/v) ethyl acetate in petroleum ether were combined and evaporated to yield 0.30 gram (45.0%) of a white oil. The white oil was found to be a 1:1 mixture of methyl 11-oxo-9-octadecenoate and methyl 8-oxo-9-octadecenoate as shown by $^1$H NMR and TLC (TLC plates were impregnated with boric acid and silver nitrate, dried and activated at 120° C. for 4 hours before use. A mixture of 10% (v/v) ether in petroleum ether was used as a mobile phase.).

YIELD

Total yield of product was 0.30 gram (45% based upon 58% conversion).

CHARACTERIZATION

The product had the following NMR spectrum.

$^1$H NMR (CDCl$_3$, 200 MHz): δ 6.83 (dtd, J=15.8, 6.6 and 2.0 Hz, 1H, olefinic), 6.12, 6.05 (dt, J=15.6 and 1.4 Hz, 1H, olefinic), 3.67 (s, 3H, OCH$_3$), 2.51 (t, 2H, CH$_2$), 2.32 (t, 2H, CH$_2$), 0.89 (t, 3H, CH$_3$).

Example 15

Oxidation of R(+) α-Pinene to R(+) α-Verbenone

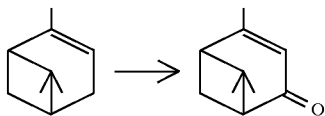

OXIDATION

R(+) α-pinene (2.8 grams, 0.0186 mol) was dissolved in a mixture of acetone (32 ml), pyridine (3 ml), and t-butyl hydroperoxide (70% aqueous solution, 20 ml). The resultant solution was stirred at room temperature and sodium periodate (6.5 grams, 0.03 mol) and water (9.0 ml) added. This reaction mixture was stirred continuously at room temperature until the reaction had run to completion (16 hours).

SEPARATION

Acetone was removed from the reaction mixture by evaporation, the residue diluted with ether (20 ml) and the ether layer washed with water. The organic layer was stirred with a sodium sulfite solution (15% aqueous solution, 100 ml) for 2 hours at room temperature, washed with water and evaporated to form a crude product.

The crude product was chromatographed on a silica gel column (70–230). The product was eluted with ethyl acetate (5% (v/v)) in hexane to yield pure R(+) α-verbenone (0.45 gram).

YIELD

Total yield of purified R(+) α-verbenone (95% purity, HPLC at 254 nm) was 0.45 gram (16%).

CHARACTERIZATION

The R(+) α-verbenone had the following NMR spectrum.

$^1$H NMR (CDCl$_3$, 200 MHz): δ 5.73 (m, 1H, 3H olefinic-H), 2.01 (d, J=1.4 Hz, 3H, CH$_3$). 1.5 (s, 3H, CH$_3$), 1.01 (s, 3H, CH$_3$).

We claim:

1. A process for effecting the allylic oxidation of an allylic compound, comprising oxidizing the allylic compound with a combination of reagents consisting essentially of an alkali metal periodate and an alkyl hydroperoxide.

2. The process of claim 1 wherein the allylic compound, alkali metal periodate and alkyl hydroperoxide are dissolved in a solvent system selected from the group consisting of (i) a water miscible organic solvent and water, and (ii) a water miscible organic solvent, a water immiscible organic solvent and water.

3. The process of claim 2 wherein the allylic compound is oxidized by the combination of alkali metal periodate and alkyl hydroperoxide in the presence of about 20% to 30% (v/v miscible) water.

4. The process of claim 1 wherein the allylic compound is an isoprenoid.

5. The process of claim 1 wherein the allylic compound is a steroid.

6. The process of claim 5 wherein the steroid is a Δ5 androstene.

7. The process of claim 6 wherein the Δ5 androstene is dehydroepiandrosterone.

8. The process of claim 1 wherein the alkali metal periodate is sodiun periodate.

9. The process of claim 1 wherein the alkyl hydroperoxide is butyl hydroperoxide.

10. The process of claim 1 wherein the isoprenoid is oxidized by the combination of alkali metal periodate and alkyl hydroperoxide at a temperature of between about 20° to 35° C.

11. A process for allylically oxidizing an allylic compound, comprising:

(a) dissolving an allylic compound in an organic solvent, (b) adding reagents consisting essentially of an alkali metal periodate and an alkyl hydroperoxide to the allylic compound under conditions effective for achieving allylic oxidation of the allylic compound, and (c) separating the allylically oxidized allylic compound from the organic solvent.

12. The process of claim 11 further comprising incorporating water into the organic solvent.

13. The process of claim 12 wherein the organic solvent comprises an organic solvent system comprising a water miscible organic solvent and a water immiscible organic solvent, and about 20% to 30% (v/v miscible) water is added to the organic solvent system.

14. The process of claim 11 wherein the allylic compound is an isoprenoid.

15. The process of claim 11 wherein the allylic compound is a steroid.

16. The process of claim 15 wherein the steroid is a Δ5 androstene.

17. The process of claim 16 wherein the Δ5 androstene is dehydroepiandrosterone.

18. The process of claim 11 wherein the alkali metal periodate is sodium periodate.

19. The process of claim 18 wherein the alkyl hydroperoxide is t-butyl hydroperoxide, and the blend of allylic compound, sodium periodate and t-butyl hydroperoxide is maintained at a temperature of between about 20° to 35° C.

* * * * *

UNITED STATES PATENT AND TRADEMARK OFFICE
CERTIFICATE OF CORRECTION

PATENT NO. : 5,869,709

DATED : February 9, 1999

INVENTOR(S) : Marwah et al.

It is certified that error appears in the above-identified patent and that said Letters Patent is hereby corrected as shown below:

Table 1, Line 2, replace "5.1" with --5.2--

Table 1, Line 8, replace "COCH3" with --COCH$_3$--

Table 1, No. 5 Formula, replace solid arrow with OH should be lined arrow

Column 15, Line 65, replace "4,72" with --4.72--

Column 18, Line 22, replace "-CH$_3$" with --CH$_3$--

Column 18, Line 23-25, replace "↓" with --✶--

Column 18, Line 27, replace "6CH2CH" with --6CH$_2$CH--

Column 19, Line 34, replace "CH$_3$)." with --CH$_3$),--

Signed and Sealed this

Thirteenth Day of July, 1999

Q. TODD DICKINSON

*Attest:*

*Attesting Officer*         Acting Commissioner of Patents and Trademarks